(12) United States Patent
Gordon et al.

(10) Patent No.: US 9,295,851 B2
(45) Date of Patent: Mar. 29, 2016

(54) IMPLANTABLE MEDICAL DEVICE HAVING POWER SUPPLY FOR GENERATING A REGULATED POWER SUPPLY

(71) Applicant: Medtronic, Inc., Minneapolis, MN (US)

(72) Inventors: Charles R Gordon, Phoenix, AZ (US); Shohan T Hossain, Maple Grove, MN (US); Weizheng Liang, Chandler, AZ (US); James D Reinke, Maple Grove, MN (US); Gregg T Sarkinen, Montrose, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/679,763

(22) Filed: Apr. 6, 2015

(65) Prior Publication Data

US 2015/0251010 A1    Sep. 10, 2015

Related U.S. Application Data

(62) Division of application No. 13/871,013, filed on Apr. 26, 2013, now Pat. No. 9,002,447.

(51) Int. Cl.
*A61N 1/37* (2006.01)
*A61N 1/378* (2006.01)
*A61N 1/02* (2006.01)

(52) U.S. Cl.
CPC ............... *A61N 1/378* (2013.01); *A61N 1/025* (2013.01)

(58) Field of Classification Search
None
See application file for complete search history.

(56) References Cited

U.S. PATENT DOCUMENTS

| | | | |
|---|---|---|---|
| 6,115,272 A | 9/2000 | Pasternak | |
| 6,198,645 B1 | 3/2001 | Kotowski et al. | |
| 6,469,554 B1 | 10/2002 | Harpham | |
| 6,472,926 B2 | 10/2002 | Taito et al. | |
| 6,563,235 B1 | 5/2003 | McIntyre et al. | |
| 7,184,833 B2 | 2/2007 | Ganion et al. | |
| 7,622,984 B2 | 11/2009 | Lesso et al. | |
| 7,923,865 B2 | 4/2011 | Melse | |
| 8,089,787 B2 | 1/2012 | Melse | |
| 9,002,447 B2 | 4/2015 | Gordon et al. | |
| 2004/0167407 A1 | 8/2004 | Roberts | |
| 2004/0179547 A1 | 9/2004 | Kuffner et al. | |
| 2006/0271110 A1 | 11/2006 | Vernon et al. | |
| 2009/0259278 A1 | 10/2009 | Torgerson et al. | |
| 2010/0264890 A1 | 10/2010 | Caldwell | |

OTHER PUBLICATIONS

U.S. Appl. No. 61/782,093, "Implantable Medical Device Having Power Supply for Generating a Regulated Power Supply".
U.S. Appl. No. 61/781,982, "Implantable Medical Device Having a Power Supply for Generating a Regulated Power Supply".

*Primary Examiner* — Brian T Gedeon
*Assistant Examiner* — Ankit Tejani
(74) *Attorney, Agent, or Firm* — Evans M. Mburu (57) ABSTRACT

A device for generating a plurality of output voltages from a single input energy supply source is described. The device includes a switched capacitor voltage converter that provides each of the output voltages having different supply ratios. The supply ratio is defined as a function of the input voltage provided to the switched capacitor voltage converter by the energy supply source. The switched capacitor voltage converter includes a plurality of capacitors selectively coupled to a plurality of switches that dynamically configure the capacitors into a plurality of stacked configurations. Switching between the plurality of stacked configurations may be controlled based on predetermined criteria.

13 Claims, 8 Drawing Sheets

Mode A

Configuration 1

Configuration 2

Configuration 3

FIG. 5A

Mode B

Configuration 4

Configuration 5

Configuration 6

FIG. 5B

Mode C

Configuration 7

Configuration 8

FIG. 5C

TABLE 1

| SUPPLY RATIO (K) | CONFIGURATION | S1A | S1C | S1D | S1E | S2A | S2C | S2D | S2E | S2F | S3A | S3B | S3C | S12 |
|---|---|---|---|---|---|---|---|---|---|---|---|---|---|---|
| K = 2/3, 1/3 | 1 | 1 | 0 | 0 | 1 | 1 | 0 | 0 | 1 | 0 | 0 | 0 | 0 | 0 |
| K = 2/3, 1/3 | 2 | 0 | 1 | 0 | 0 | 0 | 0 | 1 | 0 | 1 | 0 | 0 | 0 | 0 |
| K = 2/3, 1/3 | 3 | 0 | 1 | 0 | 0 | 0 | 1 | 0 | 0 | 0 | 1 | 1 | 0 | 0 |
| K = 3/4, 1/2 | 4 | 0 | 1 | 0 | 0 | 1 | 0 | 0 | 1 | 0 | 0 | 0 | 0 | 0 |
| K = 3/4, 1/2 | 5 | 1 | 1 | 0 | 0 | 0 | 0 | 1 | 0 | 0 | 0 | 0 | 0 | 1 |
| K = 3/4, 1/2 | 6 | 0 | 0 | 0 | 0 | 0 | 0 | 1 | 0 | 0 | 1 | 0 | 0 | 0 |
| K = 1, 1/2 | 7 | 1 | 1 | 1 | 0 | 1 | 1 | 0 | 0 | 1 | 0 | 0 | 0 | 0 |
| K = 1, 1/2 | 8 | 0 | 1 | 0 | 0 | 0 | 1 | 0 | 0 | 0 | 0 | 1 | 1 | 0 |

FIG. 6

IMPLANTABLE MEDICAL DEVICE HAVING POWER SUPPLY FOR GENERATING A REGULATED POWER SUPPLY

RELATED APPLICATION

This application is a divisional of U.S. patent application Ser. No. 13/871,013, filed Apr. 26, 2013 entitled "IMPLANTABLE MEDICAL DEVICE HAVING POWER SUPPLY FOR GENERATING A REGULATED POWER SUPPLY", now U.S. Pat. No. 9,002,447 issued on Apr. 7, 2015, herein incorporated by reference in its entirety.

FIELD

This disclosure relates generally to implantable medical devices, and more particularly to circuits and techniques for optimizing power consumption.

BACKGROUND

Implantable devices exist that electrically stimulate body tissue to treat or relieve the symptoms of a wide variety of physiological or psychological maladies. Such devices are typically part of systems that are entirely implantable within the patient or are partially implantable and partially external to the patient. Systems that are entirely implantable in the patient typically include an implantable medical device some of which may have medical leads for sensing and therapy delivery functions. In such a system, the implantable medical device is entirely implanted in the bodies of the patients.

Such implantable devices are often powered by an internal power source, such as a battery, to power the device functions continuously over a long period of time. Often for implantable medical devices, the power source used to power the device's circuitry is non-rechargeable. The power source is included in the implantable device, which in turn is surgically implanted and is typically intended to be physically inaccessible. As such, the longevity of the device is a function of the rate of depletion of the battery, which may range from approximately three (3) years to approximately eight (8) years based upon the usage of the stored charge.

There remains a need for techniques to optimize the consumption of the charge stored by the power source to extend the device longevity.

SUMMARY

Generally, the disclosure pertains to optimization of power consumption by an implantable medical device ("IMD"). The disclosure may be embodied in an IMD of the type having electronic circuitry for performing monitoring of a physiologic state and/or therapy delivery under the control of a control unit such, for example, as a microcontroller or microprocessor. In order to extend the life of the IMD, it is generally desired to reduce the power consumption of the electronic circuitry. One such reduction can be achieved by providing power to the electronic circuitry having several different voltage levels such that only a necessary voltage level is delivered to each portion of the circuit.

Accordingly, one embodiment includes a power supply for concurrently generating a plurality of output voltages from a single input voltage. The power supply includes a plurality of capacitors that are coupled to a switch array having a plurality of switches. The plurality of capacitors are dynamically configurable in at least a first and a second mode to generate multiple output voltages. Each of the first and second modes is defined by at least two separate stacked configurations of the plurality of capacitors. Each of the modes establishes separate supply ratios for the plurality of output voltages supplied to loads that are coupled to the charge pump.

In an embodiment, a power supply includes first and second floating capacitors that are coupled to third and fourth hold capacitors through the plurality of switches. Each of the hold capacitors is coupled to a separate load, and the loads are individually supplied with regulated output voltages based on charge drawn from the power source. In some embodiments the regulated output voltages have separate supply ratios. Each of the plurality of switches is operable in one of multiple states to selectively configure the floating and hold capacitors in the at least two stacked configurations associated with each of the first and second modes.

In any one of the modes, the stacking of the floating and hold capacitors may be alternated between the predefined stacked configurations associated with the selected mode to provide the plurality of output voltages having preselected supply ratios to loads that are coupled to each of the third and fourth hold capacitors.

In some embodiments, the frequency of alternating between the stacked configurations associated with the selected mode is varied in response the load coupled to the hold capacitors. The frequency may be increased based on an increase in the energy demands of the loads to generate more power. In other embodiments, the frequency is varied as a function of the residual amount of charge stored in the power source. In other embodiments, the frequency may be increased in response to depletion of the charge stored by the power source.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

Illustrative embodiments of the disclosure are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Some patient disorders may be treated via delivery of stimulation to a target tissue site within the patient. For example, an implantable medical device ("IMD") may be implanted within the patient and positioned to deliver electrical stimulation to the target tissue site via a plurality of electrodes.

Figure 1:
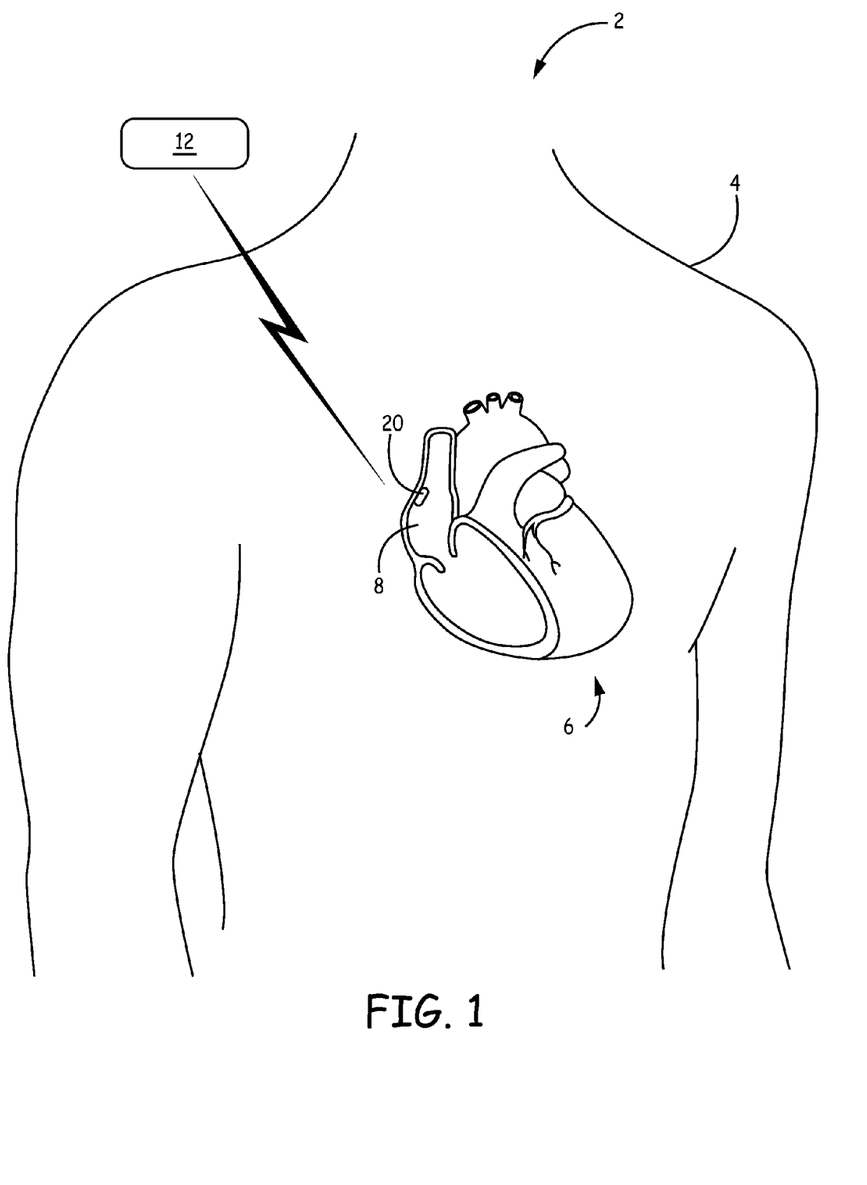
FIG. 1 is a conceptual diagram illustrating an example therapy system for treating a cardiac disorder of a patient.

FIG. 1 is a conceptual diagram illustrating an example therapy system 2 for treating a cardiac disorder of patient 4. System 2 includes leadless IMD 20 and external interrogation device 12, which may communicate with one another, e.g., via wireless telemetry. In the example illustrated in FIG. 1, external interrogation device 12 may be an external programmer and leadless IMD 20 is implanted within right atrium 8 of heart 6 of patient 4, proximate to the sinoatrial (SA) node of patient 4. In other examples, leadless IMD 20 may be implanted proximate to another portion of heart 6 of patient 4.

Leadless IMD 20 may provide one or more advantages. For example, a leadless IMD may eliminate the need for an implantable lead, and may also require a smaller power source such that a stimulator of the IMD may be positioned directly at the target tissue site. Example leadless pacemakers and neurological stimulators are described in, for example, U.S. Pat. No. 3,943,936 which issued to Rasor et al. on Mar. 16, 1976, entitled "Self Powered Pacers and Stimulators," and which is incorporated herein by reference in its entirety.

Although the example systems and techniques are primarily described herein with respect to delivering electrical stimulation to the target tissue site via a plurality of housing electrodes, in other examples, the systems and techniques may be applicable to other types of stimulation of the target tissue site. In addition, although the example systems and techniques are primarily described herein with respect to delivering electrical stimulation to a target tissue site within or on heart 6 of patient 4 to treat a cardiac disorder, in other examples, the systems and techniques may be applicable to stimulation of other types of target tissue sites. For example, the systems and techniques may be utilized to excite cells that are found in skeletal, smooth muscle, pancreatic, and neural tissue. In some examples, the systems and techniques described herein are applicable to deep brain stimulation for the treatment of Parkinson's disease or stimulation of the spinal cord or peripheral nerves for the treatment of pain. In some examples, the systems and techniques described herein may be used to deliver stimulation to target tissue sites within the brain or spinal cord of patient 4, gastrointestinal tissue to support gastrointestinal therapy such as therapy to address obesity, motility disorders (e.g., gastroparesis), dyspepsia, or other therapies, pelvic floor tissue (e.g., sacral or pudendal nerve tissue) to support pelvic floor therapy such as pain therapy, urinary or fecal incontinence therapy, sexual dysfunction, or other therapies, or cranial tissue to support cranial nerve therapy such as therapy to relieve occipital neuralgia, trigeminal neuralgia, facial pain, migraine headaches, other target nerves of patient 4, and the like.

Leadless IMD 20 includes a housing and a stimulation energy delivery element positioned on the housing or within the housing and controlled by a stimulation module to deliver stimulation to a target tissue site. In addition, leadless IMD 20 may include a pump reservoir within the housing that stores genetic material and a pump within the housing that delivers the genetic material to the target tissue site. Delivery of genetic material to the target tissue site can improve properties of cells of the target tissue site to increase the efficiency of treatment of the disorder of patient 4. The genetic material delivered to the target tissue site via the pump of IMD 20 may take any suitable form. In some examples, the genetic material may be delivered via a viral vector, such as an adenoviral or adeno-associated viral vector.

In the example illustrated in FIG. 1, IMD 20 is positioned proximate to the SA node of heart 6 of patient 4. When functioning normally, the SA node of heart 6 is the pacemaker for heart 6 and generates action potentials that establish a normal rhythm of heart 6. However, when the SA node of patient 12 functions abnormally, patient 12 may require therapy and/or treatment to maintain a normal sinus rhythm of heart 6. For example, IMD 20 may deliver electrical stimulation to heart 6 to pace heart 6.

Ultimately, it is desirable to treat a patient's condition for his or her lifetime. But the implanted medical devices such as IMD 20 generally rely on a finite power source, such as a non-rechargeable battery, to provide energy for delivery of therapeutic stimulation. The timing of the depletion of the power source is often unpredictable and will vary from patient to patient because it is highly dependent on frequency of usage. Moreover, when the power source of the implanted medical device is depleted, it may not be desirable or possible to explant the medical device. As such, a need exists to extend the longevity of the IMD 20 to reduce the number of implant procedures for subsequent devices.

In addition to leadless IMD 20, system 2 includes interrogation device 12, which communicates with leadless IMD 20. In some examples, interrogation device 12 may comprise a handheld computing device, computer workstation, or networked computing device. Interrogation device 12 includes a user interface that presents information to and receives input from a user. It should be noted that the user may also interact with interrogation device 12 remotely via a networked computing device. The interrogation device 12 may have external programming capabilities that provide options for manually conducting stimulation threshold tests and reprogramming the stimulation parameters in order to minimize the required stimulation energy. In addition, the user may interact with interrogation device 12 to retrieve physiological or diagnostic information from leadless IMD 20. A user may also interact with interrogation device 12 to program leadless IMD 20, e.g., select values for operational parameters of leadless IMD 20.

IMD 20 and interrogation device 12 may communicate via wireless communication using any techniques known in the art. Examples of communication techniques may include, for example, inductive coupling, or low frequency, or radiofrequency (RF) telemetry, or a combination thereof, with other techniques also being contemplated.

The IMD 20 includes electronic circuitry that is operable to perform a therapeutic and/or monitoring function of a patient 4. In addition, the IMD 20 includes a power supply that provides the various components of the IMD 20 with energy to enable functionality.

Figure 2:
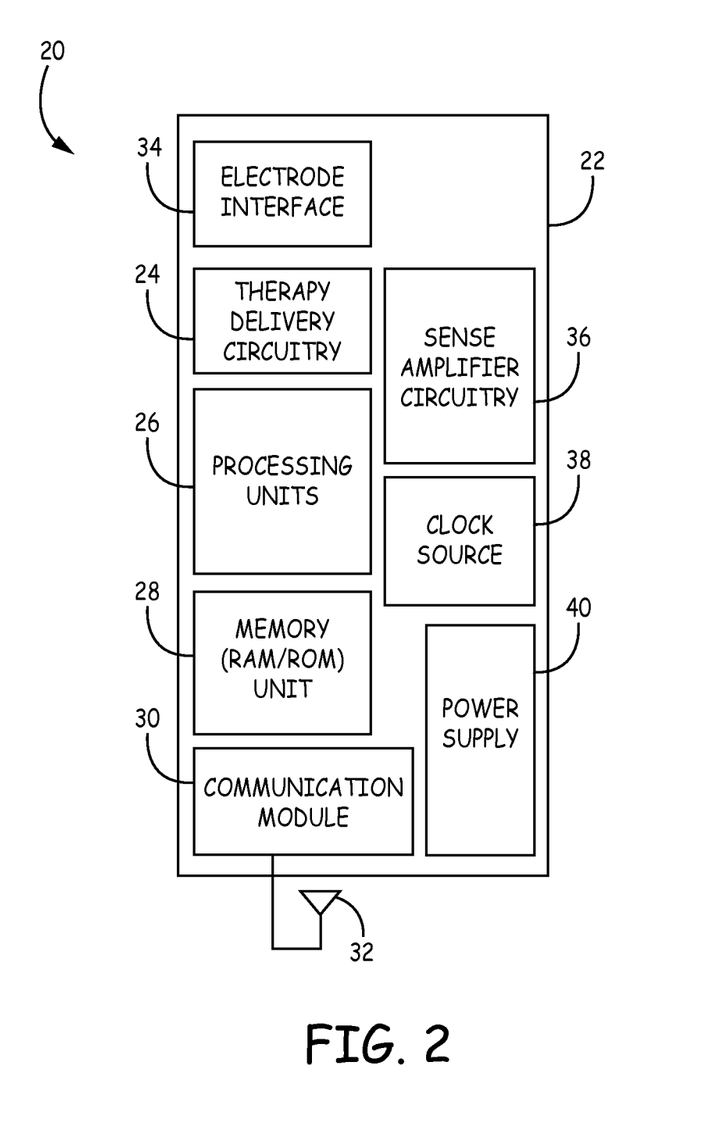
FIG. 2 is a block diagram of example circuitry of an IMD suitable for use in the system depicted in FIG. 1.

FIG. 2 shows an exemplary block diagram of some components within an IMD 20 configured in accordance with certain embodiments of the invention. As can be seen from FIG. 2, IMD 20 includes primary electronic circuitry 22 for managing the operation and function of IMD 20, with such electronic circuitry 22 being contained within a hermetic enclosure of IMD 20. The electronic circuitry 22 includes a number of electrical components, most of which are exemplified in U.S. Pat. No. 6,539,253, entitled "Implantable Medical Device Incorporating Integrated Circuit Notch Filters" (incorporated herein by reference in relevant part). In certain embodiments, the electronic circuitry 22 in FIG. 2 includes, without limitation: sense amplifier circuitry 36; therapy delivery circuitry 24; a clock source 38; a suitable amount of memory 28, which may include random-access memory (RAM) and/or read-only memory (ROM); processing unit(s) 26; and a power supply 40. In certain embodiments, the electronic circuitry 22 also includes a communication module 30 and one or more antennas 32 configured to enable IMD 20 to communicate with other devices within and/or outside the body area network. It should be appreciated that the below descriptions of the electronic circuitry 22 within the IMD 20 are merely example configurations.

In certain embodiments, when IMD 20 is used for cardiac applications (e.g., to provide cardiac sensing and pacing functions for the patient), the IMD 20 may be coupled to one or more medical leads (not shown) which, when implanted, extend transvenously between the implant site of the IMD 20 and the patient's heart. Also not shown in FIG. 2 is the protection circuitry commonly included in implanted devices to protect, for example, the sensing circuitry of the device from high voltage stimulating pulses.

An electrode interface 34 may be provided to electrically couple one or more electrodes from an external surface, or extension thereto, for therapy delivery and/or monitoring functions.

As previously noted, the electronic circuitry 22 includes the processing unit 26 which generally varies in sophistication and complexity depending upon the type and functional features of the IMD 20. In certain embodiments, the processing unit 26 can be an off-the-shelf programmable microprocessor, a microcontroller, a custom integrated circuit, or any of a wide variety of other implementations generally known. Although specific connections between the processing unit 26 and other components of the IMD 20 are not shown in FIG. 2, it will be apparent to those of ordinary skill in the art that the processing unit 26 functions to control the timed operation of the sense amplifier circuitry 36 and the therapy delivery circuitry 24. In certain embodiments, the functioning of the processing unit 26 would be under control of firmware and programmed software algorithms stored in memory 28 (e.g., RAM, ROM, PROM and/or reprogrammable ROM) and are carried out using a processing unit of a typical microprocessor core architecture. In certain embodiments, the processing unit 26 can also include a watchdog circuit, a state machine, a DMA controller, a lock mover/reader, a CRC calculator, and other specific logic circuitry coupled together by on-chip bus, address bus, and power, clock, and control signal lines in paths or trees in a manner well known in the art.

In certain embodiments, the power supply 40 powers the electronic circuitry 22 and can also be used to power electromechanical devices, such as valves or pumps, of a substance delivery IMD, or to provide electrical stimulation energy of an ICD shock generator, cardiac pacing pulse generator, or other electrical stimulation generator. In certain embodiments, the power supply 40 is a high energy density, low voltage battery. The power supply circuit provides one or more low voltage power supply signals, one or more voltage reference sources, current sources, and, in the case of an ICD, high voltage power to the therapy delivery circuitry 24. For the sake of clarity in the example block diagram provided in FIG. 2, the connections between the power supply 40 and the electrical components of the IMD 20 are not shown, as one skilled in the art would be familiar with such connections.

In certain embodiments, the sense amplifier circuitry 36 can be configured to process physiologic signals that are used to trigger or modulate therapy delivery and are stored as physiologic signal data for later retrieval as described herein. Generally, the sense amplifier circuitry 36 is coupled to electrical signal sense electrodes and/or physiologic sensors on or in the housing of the IMD 20 or as mentioned above, situated at sites distanced from the IMD housing, typically in distal portions of a medical lead. As such, in some cardiac applications, the sense amplifier circuitry 36 is designed to receive electrical cardiac signals from the electrodes and/or sensors and to process such signals to derive event signals reflecting the occurrence of specific cardiac electrical events, including atrial contractions (P-waves) and ventricular contractions (R-waves). These event-indicating signals are provided to the processing unit 26 for use in controlling the synchronous stimulating operations of the IMD 20 in accordance with common practice in the art. In addition, these event indicating signals may be communicated, via uplink transmission, to one or more external communication devices.

In example embodiments, the therapy delivery circuitry 24 can be configured to deliver electrical stimulation to the patient, e.g., cardioversion/defibrillation therapy pulses and/or cardiac pacing pulses delivered to the heart, or other electrical stimulation delivered to the brain, other organs, selected nerves, the spinal column, the cochlea, or muscle groups, including skeletal muscle wrapped about the heart.

Registers of the memory 28 can be used for storing data compiled from sensed cardiac activity and/or relating to device operation. Generally, the data storage can be triggered manually by the patient, on a periodic basis, or by detection logic (e.g., within the sense amplifier circuitry 36) upon satisfaction of certain programmed-in event detection criteria.

Memory 28 may also be used to store data necessary to support the power generation techniques described herein. For example, various threshold and/or predetermined values levels, triggers, ratios, and other parameters associated the configuration of the power supply 40 may be stored in the memory. The memory may also be configured to store instructions and control signals pertaining to generating the plurality of output voltages.

In certain embodiments, the clock source 38 generally employs clocked CMOS digital logic ICs having a clock signal provided by a crystal (e.g., piezoelectric) and a system clock coupled thereto as well as discrete components, e.g., inductors, capacitors, transformers, high voltage protection diodes, and the like that are mounted with the ICs to one or more substrate or printed circuit board. In certain embodiments, the system clock provides one or more fixed frequency clock signals that are independent of the battery voltage over an operating battery voltage range for system timing and control functions and in formatting telemetry signal transmissions. Again, the lines over which such clocking signals are provided to the various timed components of the IMD 20 (e.g., processing unit 26) are omitted from FIG. 2 for the sake of clarity.

In certain embodiments, the IMD 20 can involve an implantable cardiac monitor without therapy delivery system 24, e.g., an implantable EGM monitor for recording the cardiac electrogram from electrodes remote from the heart as disclosed in U.S. Pat. No. 5,331,966. Alternatively, the IMD 20 can involve an implantable hemodynamic monitor ("IHM") for recording cardiac electrogram and other physiologic sensor derived signals, e.g., one or more of blood pressure, blood gases, temperature, electrical impedance of the heart and/or chest, and patient activity.

Those of ordinary skill in the art will appreciate that IMD 20 may include numerous other components and subsystems, for example, activity sensors and associated circuitry. The presence or absence of such additional components in IMD 20, however, is not believed to be pertinent to the present invention, which relates to optimizing power consumption. It is desirable to reduce the size of the IMD 20 while increasing its functional capabilities and prolonging battery life to increase longevity. In this regard, IMD 20 may be suitably configured to adjust its power characteristics as needed in response to information related to the energy demands of the load or depletion of the energy source.

Figure 3:
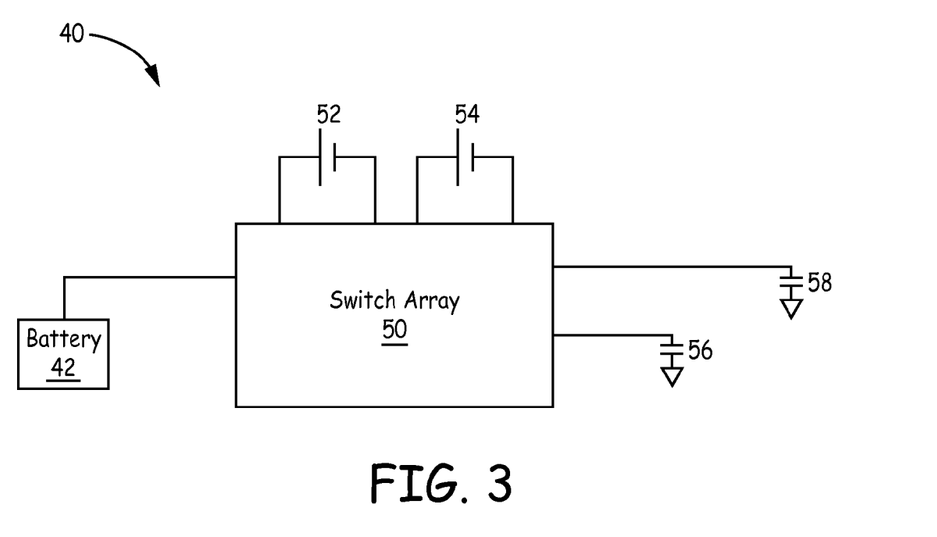
FIG. 3 depicts components of power supply in accordance with an embodiment of the disclosure.

FIG. 3 depicts components of power supply 40 in accordance with an embodiment of the disclosure. The power supply 40 is embodied as a switched capacitor voltage regulator that includes various components for concurrently generating a plurality of output voltages based on a single input voltage. The power supply 40 may include any number of devices or software components (active or passive) to maintain each of the output voltages within a range of predetermined parameters such as current, voltage, etc.

A switch array 50 is electrically coupled to a power source from which a single voltage is supplied. The power source may include a rechargeable or non-rechargeable charge storage component. In the example of IMD 20, the charge storage component includes a non-rechargeable battery 42 having an expected operating life of about 3 to 10 years based on the energy demands of the electronic circuitry 22 and the therapy and/or monitoring functions. In other words, the operating life of the battery 42 is based on the rate of depletion of the stored charge by the electronic circuitry 22 and the therapy and monitoring functions. In general, a longer battery life is desirable although this is limited by the storage capacity due at least in part to the physical size restraints of the battery 42. As such, the inventors have provided techniques for reducing the power consumption of the battery's limited charge by the electronic circuitry 22 to extend the longevity of IMD 20.

Power supply 40 simultaneously generates a power supply having two or more regulated output voltages that are provided to multiple portions of the electronic circuitry 22 of the IMD 20. Accordingly, switch array 50 is coupled to a plurality of capacitors such, for example, as capacitors 52, 54, 56, and 58 in the depicted embodiment. As will be discussed with reference to FIG. 4, some of the capacitors 52-58 are designated as floating capacitors and the rest are designated as the hold capacitors. The floating capacitors are coupled to the battery 42 while each of the hold capacitors is coupled to a load. In most cases, the hold capacitors are not shared among the loads, but rather, each individual load is coupled to one of the hold capacitors. On the other hand, the floating capacitors are selectively coupled to the battery 42 to obtain charge stored by the battery 42. The floating capacitors and hold capacitors are dynamically stacked in various orientations.

Figure 4:
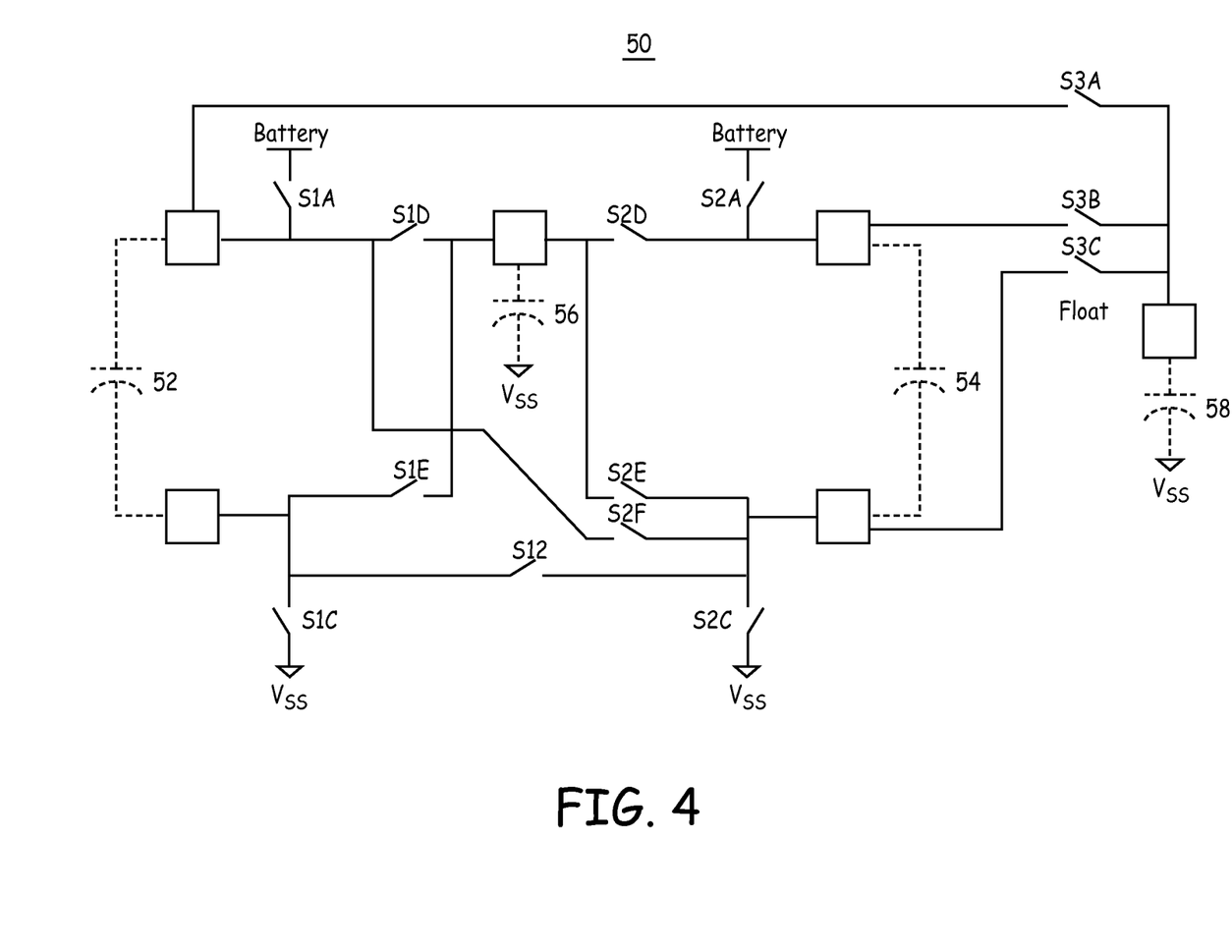
FIG. 4 depicts an embodiment of a switch array of the power supply of FIG. 3.

Turning to FIG. 4, one embodiment of the switch array 50 is depicted. For completeness, the capacitors 52-58 are depicted in phantom lines to better illustrate the components of the power supply 50. In accordance with one implementation, capacitor 52 is defined as a first floating capacitor, capacitor 54 is defined as a second floating capacitor, capacitor 56 is defined as a third hold capacitor and capacitor 58 is defined as a fourth hold capacitor. The floating capacitors are coupled to the hold capacitors by the switch array 50 that includes a plurality of switches including, for example, as S1A, S1C, S1D, S1E, (collectively, "S1"), S2A, S2C, S2D, S2E, S2F (collectively, "S2"), and S3A, S3B, S3C (collectively "S3"). The plurality of switches may comprise solid state switches with low impedance such as Field Effect Transistor (FET) switches.

The plurality of switches have multiple states and are selectively controlled between the states to dynamically stack the capacitors 52-58 in one of a plurality of stacked configurations. In other words, operation of the switches in one of the states establishes the stacked configuration of the plurality of capacitors. For example, the capacitors 52-58 may be arranged in parallel, series, or combination parallel and series configuration as viewed between the battery 42 and an output node of the power supply 40. It should be noted that one or more of the plurality of capacitors may remain unconnected in one or more of the stacked configurations.

In the example implementation, two regulated output voltages may be generated with a first output voltage being provided to a first portion of the electronic circuitry 22 having analog circuitry and a second output voltage being provided to a second portion of the electronic circuitry 22 having digital circuitry. For simplicity, the component(s) in each of the first and second portions will be referred to as a load. Each of the hold capacitors is electrically coupled to one or more of the aforementioned loads to provide appropriate output voltages associated with each of the loads.

The different loads may have differing energy requirements and consistent with aspects of this disclosure, the two regulated output voltages may be generated having voltage levels that are defined to meet the differing energy requirements of the loads. For example, the first output voltage may be greater than the second output voltage with each of the two values being set based on the requirements of the associated component(s) and/or circuitry in each of the loads. As one example, the first output voltage may have a value that is two times the value of the second output voltage.

In accordance with further aspects of the disclosure, the plurality of regulated output voltages generated by the power supply 40 have differing ratios, computed relative to the single input voltage. Each of these ratios is herein referred to as a supply ratio. In its simplest form, the supply ratio for each of the regulated output voltages may be defined as the proportion of the output voltage to the input voltage ($V_O/V_{in}$). Specific supply ratios may be established as a function of the stacked configuration of the plurality of capacitors between the input and a selected one of the output nodes. The supply ratios may be any fraction of the voltage of battery 42 including fractions that yield a higher voltage or fractions that yield a lower voltage relative to the voltage of battery 42.

Continuing with the exemplary embodiment of FIG. 4, the two output voltages generated may each have a different supply ratio. For example, if the floating capacitors 52, 54 are charged across battery 42 in parallel and subsequently coupled to a hold capacitor (e.g., 56) in series, the corresponding output voltage (as discharged across a load coupled to capacitor 56) is double of the voltage of battery 42. If the floating capacitors 52, 54 are charged across battery 42 in series and subsequently discharged across the load in parallel, the corresponding output voltage is one half the voltage of battery 42. The embodiment may utilize the floating and hold capacitors in a parallel stacked configuration, a series stacked configuration, or a combination of both parallel and series stacking in order to obtain a desired voltage level to a load. Moreover, other embodiments of the disclosure can utilize other types of capacitor configurations to obtain, for example, thirds, quarters, eighths, or other fractions of the battery voltage. For simplicity, the disclosure will discuss implementations of the power supply 40 for generating voltages that are lower than the battery voltage, it being understood that the principles are equally applicable to generating voltages that are higher than the battery voltage.

Figure 5A:
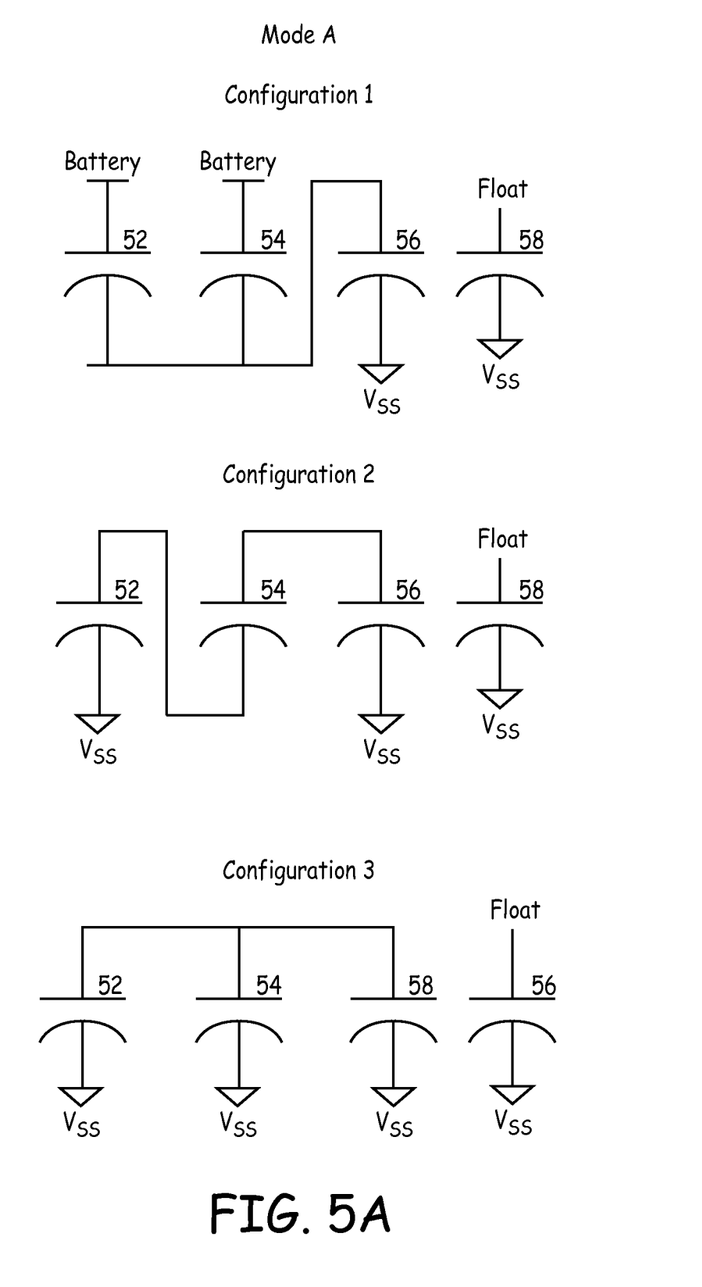
FIGS. 5A-C illustrate equivalent circuits that are established based on the dynamic configuration of a plurality of capacitors of the power supply of FIG. 4.
Figure 5B:
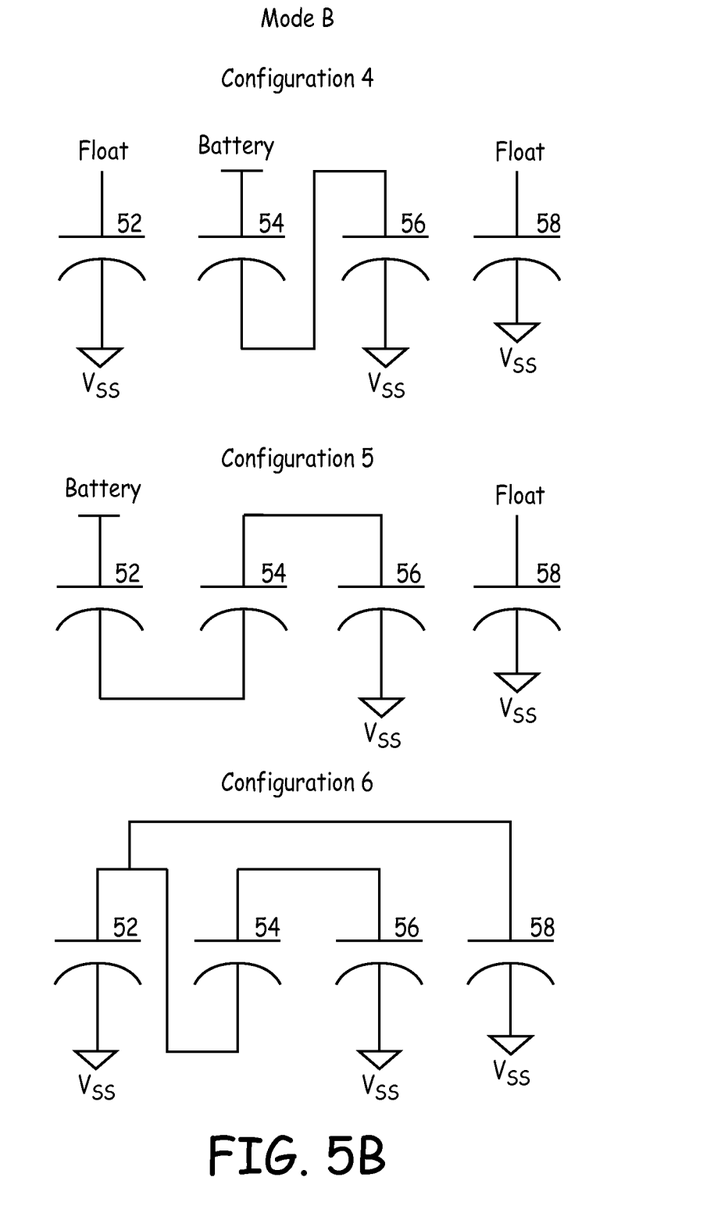
Figure 5C:
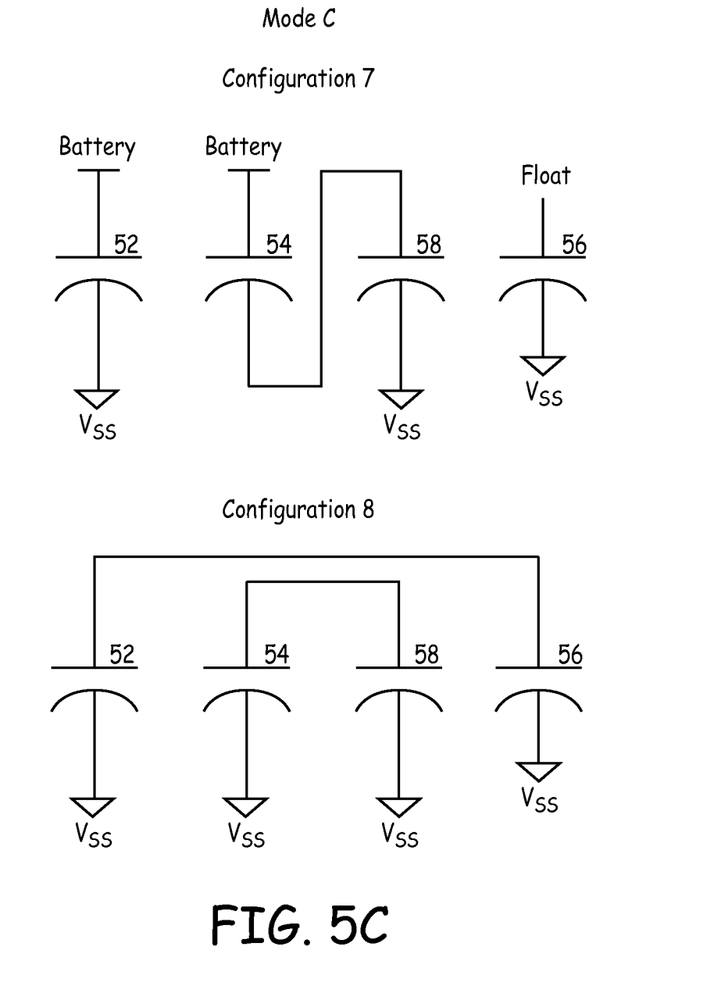

FIGS. 5A-C illustrate equivalent circuits that are established based on the dynamic configuration of the plurality of capacitors 52-58 in the embodiment of FIG. 4. The stacked configurations are achieved by selectively controlling the state of each of the plurality of switches S1, S2, and S3.

Figure 6:
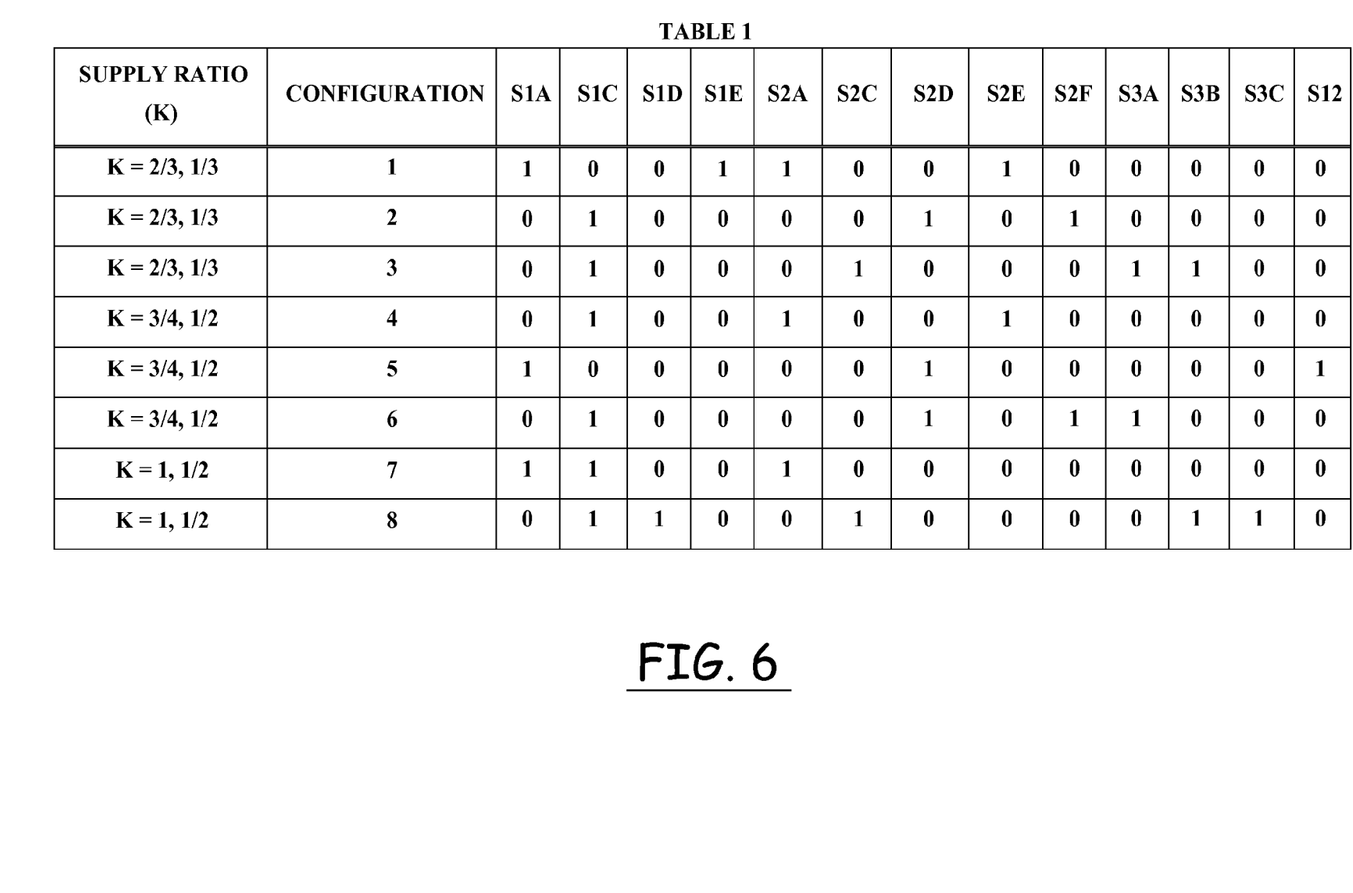
FIG. 6 depicts a table, Table 1, that outlines the various combinations of states into which a plurality of switches are placed to produce various stacked configurations of the plurality of capacitors of the power supply of FIG. 4.

FIG. 6 depicts Table 1 that outlines the various combinations of states into which the plurality of switches S1, S2, S3 are placed to produce various stacked configurations of the plurality of capacitors 52-58 in accordance with one embodiment.

In Table 1, the letter notations in the top row correspond to the similarly numbered switches in FIG. 4. Each switch may have two states: a "0" that represents an open switch and a "1" that represents a closed switch. The states of the plurality of switches illustrated in Table 1 may be embodied as software in stored in memory unit 28. The state in which each switch is placed is established by control signals that are generated by the processing units 26, for example, based on predefined criteria.

In the first column of Table 1, the supply ratios, K, of the voltage generated for each of the stacked configurations are shown. The second column indicates the stacked configurations established based on the identified switch states, while columns 3 to 16 indicate the state to which each of the plurality of switches is set. Accordingly, each row indicates the supply ratios of the output voltage generated for the eight different stacked configurations and the associated states of the plurality of switches S1, S2, S3. The details of Table 1 are discussed with reference to and in conjunction with FIG. 4 and the equivalent shown in FIGS. 5A-C.

The plurality of capacitors are dynamically configurable in at least a first and a second mode to generate multiple output voltages. Referring to the example of Table 1, the plurality of capacitors are dynamically configured in three modes, Mode A, Mode B, and Mode C.

Each of the modes is established by coupling the floating and hold capacitors in at least two different stacked configurations as depicted in FIGS. 5A-C. Turning to FIG. 5A, Mode A is illustrated as having three different stacked configurations, Configuration 1, Configuration 2, and Configuration 3. In FIG. 5B, Mode B is illustrated as having three different stacked configurations, Configuration 4, Configuration 5, and Configuration 6. In FIG. 5C, Mode C is illustrated as having two different stacked configurations, Configuration 7 and Configuration 8. The stacked configurations associated with each mode may be predefined based on the efficiency of the power supply 40 in generating the output voltages associated with the loads.

Each of the output voltages generated in each mode has a predetermined supply ratio that may be different for each output voltage. Moreover, the supply ratios of the output voltages generated at a given hold capacitor may vary from mode to mode as illustrated, for example, in Table 1.

Control signals may be generated by a switch controller (not shown). The switch controller may be embodied, for example, as a state machine in the processing units 26 to selectively control the state of the plurality of switches S1, S2, and S3. In response to the control signals, each of the switches is selectively opened or closed as defined in Table 1 to produce the stacked configuration associated with each mode and supply ratio.

The switch controller may issue the control signals for all the switches simultaneously or in parallel to ensure that all the switches are placed in the desired state concurrently. Such a control signal may include a data stream or multiple control bits that are addressed to each of the switches. The switch controller may issue the control signals synchronized with (timed to correspond with) the edges of the clock signal generated by the crystal oscillator circuit 38. In accordance with some embodiments, the mode (e.g., Mode A, Mode B, or Mode C) within which the power supply 40 is operated is based upon predetermined criteria. As such, the control signals issued by the switch controller will maintain operation of the switch array 40 within a specified mode provided the predetermined criteria is met.

The control signals may be issued on every edge (falling, rising, or both) of the clock signal with the states of the switches being toggled to alternate the stacked configuration between the various stacked configurations associated with each of the modes. For example, the switch controller may transmit three control signals on successive clock edges (e.g., first, second and third rising clock edges) to produce the three equivalent circuits associated with Mode A as depicted in FIG. 5A. Further, three control signals may be issued on preselected clock edges to produce the three equivalent circuits associated with Mode B depicted in FIG. 5B, while two control signals may be generated on predefined clock edges to produce the two equivalent circuits associated with Mode C depicted in FIG. 5C.

In Mode A, the first control signal generated responsive to the first rising clock edge may include commands that cause the plurality of switches to open or close as defined in configuration 1 in Table 1. That is switches S1A, S1E, S2A, and S2E are closed and all the other switches (S1C-D, S2C-D, S2F, and S3A-C) are opened. On a second rising clock edge that is immediately subsequent to the first rising clock edge, the controller issues a control signal to cause switches S1C, S2D and S2F to be closed while all the other switches are opened—this is depicted in configuration 2 in Table 1. On a third rising clock edge that is immediately subsequent to the second rising clock edge, the controller issues a control signal to cause the switches S1C, S2C, S3A and S3B to be closed and all the other switches are opened—as depicted in configuration 3 in Table 1.

As a result of alternating between the three stacked configurations illustrated in FIG. 5A, two output voltages may be generated. The first output voltage has a ⅓ supply ratio while the second output voltage has a ⅔ supply ratio. The switch controller may issue control signals to sequentially alternate between configuration 1, configuration 2, and configuration 3 and continuously repeat the stacked configurations for constant supply of power by the power supply 40 to the loads.

As is depicted in Table 1, a different supply ratio is established by changing the mode. A change in the mode results in the switch controller issuing control signals that produce different stacked configurations. Again, the control signals may continuously be generated on predetermined clock edges (e.g., every rising edge, or every five edges, or every 10 falling edges) to configure the capacitors in different stacked configurations associated with each of the other modes. For example, the stacked configurations associated with Mode B are shown in FIG. 5B. The corresponding commands issued will cause toggling (opening or closing) of the switches are depicted in configurations 4, 5, and 6 in Table 1. The stacked configurations associated with Mode C are shown in FIG. 5C and the corresponding commands issued to toggle (opened or closed) the switches are depicted in configurations 7 and 8 in Table 1.

In order to conserve power, various criteria may be utilized to determine the frequency of alternating between the stacked configurations for any of the given modes, e.g., Mode A, Mode B, and Mode C. As such, the triggering clock edge for each of the modes may be predefined based on the power levels associated with each mode. For example, the frequency of control signals issued in Mode A may be synchronized with every tenth rising clock edge to cause alternating between the stacked configurations of Mode A. Continuing with that example, the frequency of issuing control signals in Mode B may be synchronized with every fifth rising clock edge, while the frequency in Mode C may be synchronized with every second rising clock edge. In accordance with embodiments of this disclosure, optimizing the frequency ensures that the power supply 40 generates only as much power as is needed to conserve the limited charge in battery 42.

The criteria may include regulating the frequency at which the control signals are issued as a function of the energy demands of the load. In other embodiments, the criteria may include the residual amount of energy stored by battery 42 while other embodiments may take into account the rate of depletion of the energy.

To illustrate, assume that the power supply 40 is operating in Mode A, and that the clock signals are being generated at a rate of 5 MHz. The plurality of capacitors are arranged in the three stacked configurations of FIG. 5A, sequentially alternating between the three configurations 1, 2, and 3 triggered by each clock edge.

As the residual amount of energy stored by battery 42 decreases or as the energy demands of the components associated with the loads coupled to hold capacitors 56 and 58 increase, the rate of the clock signals controlling the generation of the control signals by the switch controller may be increased to 10 MHz, for example. The increase in the clock signal rate causes a corresponding increase in the frequency (approximately double in this example) of alternating between the three stacked configurations 1, 2, and 3. The increase in the frequency of alternating between the stacked configurations results in an increase in the power generated by the power supply 40.

As one non-limiting example, the increased requirement for energy may be due to an increase in the volume of information to be processed by a segment of the load, such as the microprocessor. A monitoring module (not shown) may be coupled to the hold capacitors and/or the nodes connecting to the loads. In one embodiment, the monitoring module may be embodied as a brown-out detect circuit that is included in the processing unit 26. The monitoring module compares each of the plurality of output voltages generated by the power supply 40 against predetermined levels, with such predetermined levels being stored in a memory location in memory 28, for example. The monitoring module may trigger a change in the frequency responsive to detecting that the monitored output voltage is below the corresponding predetermined level. A drop in the output voltage level below the predetermined level may indicate that the power supply 40 is no longer keeping up with generation of output voltages having the desired predetermined levels or that there has been an increase in the energy demands of the load(s).

In accordance with embodiments of the disclosure, operation of the power supply 40 in a given one of the modes (Mode A, Mode B, and Mode C) may be based on predefined criteria. The predefined criteria for selecting the modes includes the level of the residual amount of energy stored by battery 42. The two or more modes, e.g., Mode A, Mode B and Mode C are defined based on preselected levels of the residual amount of energy stored by battery 42 to provide for efficient utilization of the stored charge across the entire battery life. The levels of depletion of the charge stored by the battery 42 may be expressed as a percentage of the residual charge relative to the total capacity of the battery 42.

For example, Mode A may represent a mode that provides high efficiency supply ratios for the output voltages when the charge stored is at full battery capacity until a first threshold representing about half battery capacity is reached. Mode B may represent a mode that provides mid-range efficiency supply ratios for the output voltages when the charge is less than the first threshold until a second threshold that is about a quarter of the battery capacity is reached. Continuing with the example Mode C may represent a mode that simply enables the power supply to keep up with the energy demands of the loads when the residual charge stored by the battery is less than the second threshold.

Additional criteria for selecting one of the modes may include the level of depletion of the battery charge. For example, the processing units 26 may measure the residual battery charge on a daily basis and in response to determining an increase in the rate of depletion, a mode switch may be made to improve the efficiency of generating the plurality of output voltages.

Another criteria for selecting a given one of the modes may include the power requirements of the load. For example, the mode (e.g., Mode A, Mode B, or Mode C) in which the power supply 40 is operated is selected as a function of the energy demands of the loads associated with each of the given output voltages. A monitoring module (not shown) may be coupled to the hold capacitors and/or the terminals connected to the loads. In one embodiment, the monitoring module may be embodied as a brown-out detect circuit that is included in the processing unit 26. The monitoring module compares each of the plurality of output voltages generated by the power supply 40 against predetermined levels, with such predetermined levels being stored in a memory location in memory 28 for example. The monitoring module may trigger a change in the mode in response to detecting that the monitored output voltage is below the corresponding predetermined level. A fall in the output voltage level may indicate that the power supply 40 is no longer keeping up with generation of output voltages having the desired predetermined levels or that there has been an increase in the energy demands of the load(s).

In the foregoing description and the claims, any reference to, or designation of elements such, for example, as "first", "second", "third", and so forth is not intended to signify a numerical ordering of the elements nor is it intended to limit the number of elements. Rather, such numerical listings are merely provided to aid in the discussion.

The techniques and technologies presented herein are intended to illustrate the functional operation of an exemplary device, and should not be construed as reflective of a specific form of software, firmware or hardware necessary to practice the invention. It is believed that the particular form of software, firmware, and hardware will be determined by the particular system architecture employed in the device or system. For example, an embodiment of a system or a component may employ various integrated circuit components, e.g., memory elements, digital signal processing elements, logic elements, look-up tables, or the like, which may carry out a variety of functions under the control of one or more microprocessors or other control devices. To the extent that there is any ambiguity or inconsistency between the text and the circuit symbols depicted in the figures, the figures will be deemed to control.

Providing software, firmware and hardware to accomplish the present invention, given the disclosure herein, is within the abilities of one of skill in the art. For the sake of brevity, conventional techniques related to ventricular/atrial pressure sensing, IMD signal processing, telemetry, and other functional aspects of the systems (and the individual operating components of the systems) may not be described in detail herein. The connecting lines shown in the various figures contained herein are intended to represent example functional relationships and/or physical couplings between the various elements. It should be noted that many alternative or additional functional relationships or physical connections may be present in an embodiment of the subject matter.

For the sake of brevity, conventional techniques and features related to IMDs, IMD telemetry, signal processing, data transmission, signaling, IMD transceivers, and other functional aspects of the systems (and the individual operating components of the systems) have not been described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

The description refers to elements or features being "connected" or "coupled" together. As used herein, unless expressly stated otherwise, "connected" means that one element/feature is directly joined to (or directly communicates with) another element/feature, and not necessarily mechanically. Likewise, unless expressly stated otherwise, "coupled" means that one element/feature is directly or indirectly joined to (or directly or indirectly communicates with) another element/feature, and not necessarily mechanically. Thus, although the figures may depict example arrangements of elements, additional intervening elements, devices, features, or components may be present in an actual embodiment (assuming that the functionality of the device/system is not adversely affected).

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

What is claimed is:

1. A regulated power supply to generate multiple output voltages based on an input voltage from a finite supply power source, comprising:
    a clock source for generating a clock signal having a plurality of frequencies;
    a plurality of capacitors dynamically configurable in a plurality of stacked configurations and operable to generate the multiple output voltages based on the input voltage;
    a switch array having a plurality of switches coupled to the plurality of capacitors and operable in a number of different states to configure the capacitors in the plurality of stacked configurations; and
    a switch controller operable to issue a control signal to control alternating between at least a first and a second of the plurality of stacked configurations as a function of a first frequency selected from the plurality of frequencies of the generated clock signal, wherein the switch controller issues the control signal to configure the plurality of capacitors in a stacked configuration selected from the plurality of stacked configurations and the alternating between each of the plurality of stacked configurations is synchronized with a clock edge.

2. The regulated power supply of claim 1, further comprising a monitoring module coupled to the plurality of capacitors and operable to compare the voltage level of the at least one of the plurality of output voltages to a predetermined voltage level and generate a conversion signal to change an operation of the switch controller from the first frequency to a second frequency.

3. The regulated power supply of claim 2, wherein in response to detecting that the output voltage level is less than the predetermined level, the second clock frequency is selected to be faster than the first clock frequency.

4. The regulated power supply of claim 2, wherein the rate of the first clock signal frequency is selected based on a residual amount of the charge stored by the power source.

5. The regulated power supply of claim 4, wherein the rate of alternating the configuration of the coupling plurality of capacitors between the at least first and second stacked configurations is increased in response to a determination that a residual amount of the stored charge is less than a predetermined value.

6. The regulated power supply of claim 2, wherein the rate of alternating between the at least first and second stacked configurations is based on a load coupled to the plurality of capacitors.

7. The regulated power supply of claim 6, wherein the rate of alternating the plurality of capacitors between the at least first and second stacked configurations is increased based on a determination that the load has exceeded a predetermined value.

8. The regulated power supply of claim 1, wherein the stacked configuration of the plurality of capacitors is alternated between the first and the second stacked configurations on successive clock edges.

9. The regulated power supply of claim 1, further comprising alternating from the second stacked configuration to a third of the plurality of stacked configurations prior to alternating back to the first stacked configuration.

10. The regulated power supply of claim 1, wherein the plurality of capacitors are stacked in at least two different stacked configurations during an adjacent first and second successive clock edges.

11. The regulated power supply of claim 10, wherein the first and second successive clock edges correspond to successive rising clock edges.

12. The regulated power supply of claim 1, wherein a rate of alternating between the at least first and second stacked configurations corresponds to the first frequency of the clock signal.

13. The regulated power supply of claim 12, wherein a faster rate of alternating is achieved by selecting a frequency of the clock signal that is faster relative to a preceding frequency of the clock signal.

* * * * *

UNITED STATES PATENT AND TRADEMARK OFFICE
CERTIFICATE OF CORRECTION

| | | |
|---|---|---|
| PATENT NO. | : 9,295,851 B2 | Page 1 of 1 |
| APPLICATION NO. | : 14/679763 | |
| DATED | : March 29, 2016 | |
| INVENTOR(S) | : Charles R. Gordon et al. | |

It is certified that error appears in the above-identified patent and that said Letters Patent is hereby corrected as shown below:

Title page, under Related U.S. Application Data, insert the following after "Division of application No. 13/871,013, filed on April 26, 2013, now Pat. No. 9,002,447":

--Provisional Application No. 61/781,982, filed March 14, 2013. Provisional Application No. 61/782,093 filed March 14, 2013.--

Signed and Sealed this
Third Day of May, 2016

Michelle K. Lee
*Director of the United States Patent and Trademark Office*